United States Patent [19]

Sharon

[11] 4,015,906
[45] Apr. 5, 1977

[54] METHOD AND APPARATUS FOR ALIGNING AN INVISIBLE BEAM PARTICULARLY A LASER BEAR

[75] Inventor: Uzi Sharon, Tel-Aviv, Israel

[73] Assignee: Laser Industries, Ltd., Tel-Aviv, Israel

[22] Filed: June 23, 1975

[21] Appl. No.: 589,591

[30] Foreign Application Priority Data

Mar. 14, 1975 Israel .................................. 46832

[52] U.S. Cl. .............................. 356/138; 350/172; 356/252

[51] Int. Cl.² .................. G02B 23/04; G02B 27/14; G02B 23/14

[58] Field of Search ... 356/123, 138, 172, 153–154, 356/251–255, 29; 331/DIG. 1; 219/121 L; 33/286; 350/172–174; 250/234

[56] References Cited

UNITED STATES PATENTS

| | | | |
|---|---|---|---|
| 3,582,215 | 6/1971 | Cornillault | 356/138 |
| 3,689,159 | 9/1972 | Taniguchi et al. | 356/123 |
| 3,752,587 | 8/1973 | Myers et al. | 356/154 |
| 3,813,170 | 5/1974 | Sears | 356/138 |
| 3,827,806 | 8/1974 | Skagerlund | 356/138 |

FOREIGN PATENTS OR APPLICATIONS

| | | | |
|---|---|---|---|
| 1,055,998 | 1/1967 | United Kingdom | 356/138 |
| 168,914 | 3/1965 | U.S.S.R. | 356/138 |

OTHER PUBLICATIONS

Bloom, A. L. "Application of CW Lasers To Surveying Precision, Optical Testing, and Alignment", Annals of the New York Academy of Sciences, vol. 122, Art. 2, pp. 658–660.

*Primary Examiner*—John K. Corbin
*Assistant Examiner*—Wm. H. Punter
*Attorney, Agent, or Firm*—Pennie & Edmonds

[57] ABSTRACT

An alignment device for aligning a beam of radiant energy, particularly a laser beam, with respect to a target comprises a reflector in the path of the beam, the reflector having an aperture of a diameter smaller than that of the beam so that the aperture permits the center portion of the beam to pass therethrough to the target, while the outer marginal fringe of the beam is intercepted and reflected to a sighting member, the device further including an optical system transposing the image of the sighting member onto the field of the target, thereby enabling real-time alignment of the beam and providing a better defined beam and while permitting the alignment to be effected before directing the beam to the target.

32 Claims, 4 Drawing Figures

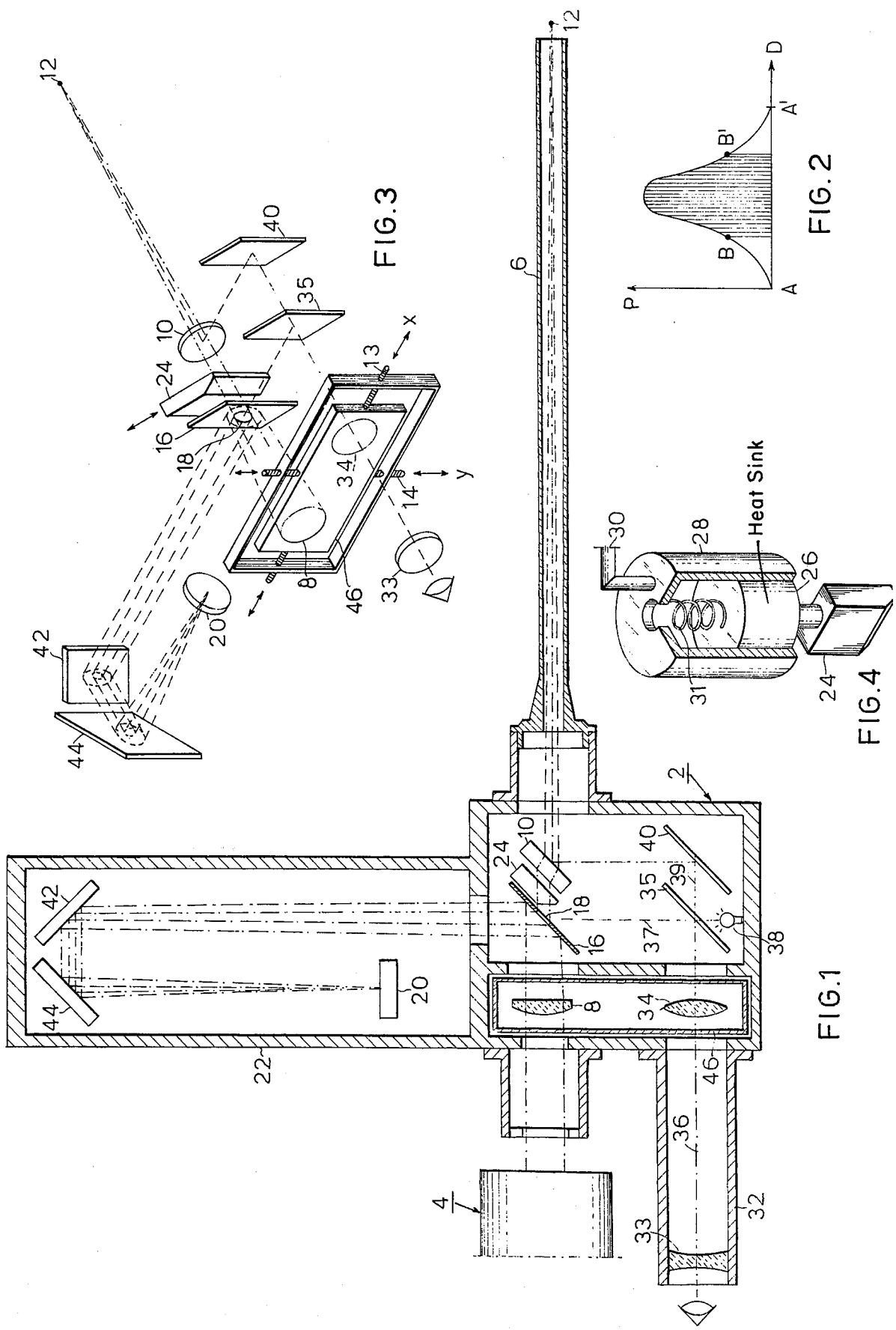

METHOD AND APPARATUS FOR ALIGNING AN INVISIBLE BEAM PARTICULARLY A LASER BEAR

BACKGROUND OF THE INVENTION

The present invention relates to alignment devices for radiant energy beams. It is particularly useful with respect to manipulatable laser beams, such as are used as laser surgical scalpels, and is therefore described below in connection with that application.

As is well known, a laser beam can be focussed to a very small spot size (e.g. 100 microns or less in diameter) to produce an extremely hot concentration of light energy. At laser wave lengths (e.g. 10.6 microns), the laser energy is almost completely absorbed by body tissue and therefore a focussed laser beam may be used to cut through most types of tissues by burning or vaporizing. One of the important advantages of using a laser beam for this purpose is that it can make very clean and fine cuts while minimizing damage to tissues outside the cutting lines. Also, the laser beam readily coagulates capillaries, small veins and small arteries, thereby minimizing loss of blood and keeping the working area clean. Because of these advantages, manipulatable laser beams are increasingly being used as surgical scalpels.

One problem, however, in using laser beams as surgical scalpels is the difficulty in precisely aligning it on target, i.e., on the spot or along the line of the cut, during the time the operation is being performed. One proposed arrangement uses a lens system which focusses the laser beam in front of the tip of the scalpel to permit viewing the working area. This arrangement includes two light sources that project two light beams which intersect at the focal point of the laser beam, to target the beam on the spot or line to be cut. Another proposed arrangement (see U.S. Pat. No. 3,659,613) includes an eyepiece for viewing the target area, and a rotatable chopper disc for alternately passing the laser beam to the target area and the viewable light to the eyepiece. Such arrangements, however, are not entirely satisfactory with respect to the precision, and the convenience of alignment and manipulation, required by a surgeon in performing delicate surgical operations.

SUMMARY OF THE INVENTION

An object of the present invention is to provide an improved alignment device for aligning radiant energy beams with respect to predetermined targets.

Another object of the invention is to provide an alignment device which is particularly useful with respect to manipulatable laser beams, and which provides a number of advantages when so used, including: real-time alignment of the laser beam; a better defined beam for producing finer and cleaner cuts; and more protection to the patient in that the patient need not be exposed to the laser beam until the alignment has been effected.

According to a broad aspect of the present invention, there is provided an alignment device for aligning a beam of radiant energy with respect to a target, the alignment device including a reflector in the path of the radiant energy beam as it travels to the target which reflector permits a portion of the beam to pass to the target while the remaining portion of the beam is intercepted and reflected. The alignment device further includes a sighting member intercepting the reflected portion of the radiant energy beam, an eyepiece, and an optical system including means interposed between the eyepiece, target, and sighting member for viewing the target and for transposing the image of the sighting member onto the field of the target as viewed via the eyepiece.

According to an additional feature, the optical system further includes a focussing lens in front of the reflector for focussing the portion of the radiant energy beam passing through the reflector to a point on the target, and for focussing the portion of the radiant energy beam intercepted by the reflector to a point on the sighting member; and means for adjusting the position of the focussing lens to simultaneously change the position of the focussed point on the target and the focussed point on the sighting member.

According to a still further feature, the reflector is formed with an aperture having a diameter smaller then the diameter of the radiant energy beam so that the aperture permits the center portion of the beam to pass therethrough to the target, while the outer marginal fringe of the beam is intercepted and reflected to the sighting member.

According to a still further feature, the radiant energy beam is a laser beam in which the major portion of the beam energy is present in the center of the beam cross-section and is focussed to a fine point on the target, while a minor portion of the beam energy is present on the outer marginal fringe and is reflected by the apertured reflector to the sighting member.

According to yet another feature the device further includes a shutter between the apertured reflector and the target; and means for selectively moving the shutter into the path of the radiant energy beam to block same from travelling to the target, or out of the path of the radiant energy beam to permit same to travel to the target.

The invention provides a number of advantages particularly important for laser scalpel applications. Thus, it permits a real-time alignment of the radiant energy beam to be made, since any adjustment of the focal point of the beam will simultaneously produce a corresponding variation in the portion of the beam intercepted by the sighting member; the image of this sighting member, as viewed by the user via the eyepiece, is transposed onto the target image, so that the user can view the adjustments with respect to the target as they are being made by the manipulation of the laser beam itself. In addition, by using only the center part of the beam for working purposes, the outer marginal fringes being used for sighting purposes, a better and more sharply defined beam is produced for working purposes. Further, since precise adjustment of the beam can be made with respect to the target before the latter is exposed to the laser beam, better protection is provided for the patient as the working area need not be exposed to the laser beam until the alignment is effected.

Further features and advantages of the invention will be apparent from the description below.

BRIEF DESCRIPTION OF THE DRAWINGS

The invention is herein described, somewhat diagrammatically and by way of example only, with reference to a preferred embodiment illustrated in the accompanying drawings, wherein:

FIG. 1 is a diagram illustrating an alignment device constructed in accordance with the invention for use particularly as a manipulatable laser type surgical scalpel;

FIG. 2 is a diagram illustrating the energy distribution in the laser beam aligned by the device of FIG. 1;

FIG. 3 is a perspective view illustrating the essential elements of the alignment device of FIG. 1; and FIG. 4 is a perspective view, partly in section, illustrating the means for moving the shutter in the device of FIG. 1.

DESCRIPTION OF THE PREFERRED EMBODIMENT

The alignment device illustrated in the drawings is particularly useful for precisely aligning a laser beam on a target before the target itself is exposed to the beam. Such devices are particularly useful as endoscope or gastroscope attachments to surgical laser scalpels for operating on the interior of hollow organs, such as the rectum, esophagus, or stomach. It is critical, as indicated earlier, that the surgeon be able to view the target to receive the laser beam, that he be able to precisely align the laser beam on the target before the target is exposed, and that a sharply defined beam be then applied on the target. All the foregoing functions are performed particularly well by the alignment device illustrated in the drawings.

As shown in FIG. 1, the alignment device includes a housing, generally designated 2, which is attachable at one end to the manipulatable laser, generally designated 4, the opposite end of the housing including a tube 6 insertable into the interior of the hollow organ to be exposed to the laser beam exiting from that end of the housing. The beam from laser 4 passes through a focussing lens 8 and a germanium window 10 before exiting through tube 6. Lens 8 focusses the beam so that it comes to a sharp focal point 12 at the outer end of tube 6, where the beam is applied to the tissue to be exposed. Germanium window 10 is transparent to the wavelength of the laser beam (in this case the beam being from a $CO_2$ laser having a 10.6 micron wavelength, as known) to permit the laser beam to pass therethrough, and is reflective with respect to other wavelengths. As shown in FIG. 3, lens 8 can be adjusted in both the X-axis as schematically shown by set screw 13, and in the Y-axis as schematically shown by set screw 14, in order to precisely align the position of the beam focal point 12 with respect to the target at the outer end of tube 6.

The present invention is directed mainly to the arrangement enabling the surgeon to make the required preliminary adjustments to align the beam precisely on the target, and to view this alignment, before exposing the patient to the laser beam. The invention provides the additional advantage, as described below, of producing a sharper and better defined beam for making very clean and fine cuts, and for minimizing damage to tissues outside the cutting lines.

The alignment device illustrated in the drawings includes an apertured reflector 16 having a center aperture 18 in the path of the laser beam as it travels from focussing lens 8 to the target at the focal point 12. Reflector 16 is at a 45° angle to this path, and its center aperture 18 is shaped so that the projection of this aperture in the vertical plane forms a circular cross-section having a diameter less than the diameter of the laser beam at that location in the path of the beam. Aperture 18 thus permits the center portion of the laser beam to pass to the target at the focal point 12, while the outer marginal fringes of the beam are intercepted by the surface of reflector 16 bordering its aperture 18.

This intercepted fringe portion of the laser beam is reflected to a sighting member 20 disposed in a tubular extension 22 of housing 2. Sighting member 20 is positioned from reflector 16 such that this intercepted and reflected portion of the laser beam also comes to a focal point thereon. Member 20 is in the form of a flat disc or screen of suitable material, such as asbestos or aluminum, which glows when impinged by a laser beam.

FIG. 2 illustrates the energy distribution of a $CO_2$ laser beam of 10.6 micron wavelength presently used in surgical lasers. The total cross-section of the beam at the location intercepted by reflector 16 is about 11mm in diameter, this being between points A,A', FIG. 2. The vertical-plane projection of aperture 18 of reflector 16 is preferably a circle of about 5mm in diameter, so that only the central portion of the beam, between points B,B', would be permitted to pass through the aperture to the target. This central portion of the beam contains the great bulk of the total beam energy, over 80%, while the outer fringe intercepted by the surface of reflector 16 bordering its aperture 18 contains only a minor portion of the beam energy, less than 20%.

It will thus be seen that the arrangement including apertured reflector 16 permits the major part of the beam energy to pass through to the target, thereby producing a sharply defined focussed beam for surgical cutting purposes, whereas the fringe of the beam, which contains a small part of the total beam energy and which would otherwise tend to blur the focussed beam on the target, is removed and is used for alignment purposes.

Disposed between apertured reflector 16 and the germanium window 10 is a shutter 24 which may be moved into blocking position to block the laser beam from proceeding to the target, or out of blocking position to permit the laser beam to pass to the target. In the embodiment illustrated in FIGS. 1 and 4, shutter 24 is carried at one end of a piston 26 movable within a cylinder 28 by the fluid pressure (e.g. air) therein as applied via an inlet tube 30, the piston moving against the action of a spring 31. The arrangement is such that spring 31 normally projects piston to bring shutter 24 into the path of the laser beam to intercept same, but when a negative pressure is applied via inlet tube 30, the piston is drawn into the cylinder moving the shutter 24 out of the path of the laser beam and permitting same to pass through window 10 to the target at the end of tube 6. Piston 26 acts as a heat sink and may be ribbed or corrugated on its outer surface to enhance the heat dissipation.

The optical system of the device illustrated further includes a microscope 32, including an eyepiece 33 and an objective lens 34, which is aligned on an axis parallel to but spaced laterally from the axis of the laser beam as it travels from the laser 4 through lens 8, apertured reflector 16, and germanium window 10 to the target at the end of tube 6. A beam-splitter 35 is disposed at the intersection of the axis 36 of microscope 32 and the line 37 passing from the sighting member 20 through aperture 18 of reflector 16. Beam splitter 35 is inclined at a 45° angle with respect to axis 36 and line 37, so that its upper surface reflects to microscope 32 the light from the sighting member 20 passing through aperture 18 of reflector 16. Underlying beam splitter 35 is an artificial light source 38 the light from which is reflected from the beam splitter along line 39 to a further reflector 40. Reflector 40 underlies germanium window 10 at the intersection of a line therefrom perpendicular to the microscope axis 36, and is disposed at an angle of 45° with respect to the microscope axis.

The light from light source 38 is transmitted, via beam splitter 35, reflector 40, and germanium window 10, to the target at the end of tube 6, the light being reflected from the target back through the same path to beam splitter 35, and then to microscope 32.

The operator can thus view the target area by looking through the eyepiece, and at the same time he will see the image of the sighting member 20 transposed on the target.

For the sake of compactness a folded reflector system, including reflectors 42, 44, is used between sighting member 20 and apertured reflector 18. Also to minimize parallax when adjusting the focussing lens 8 via screws 13, 14 (FIG. 3), the objective lens 34 of microscope 32 is mechanically coupled to the focussing lens, as by being mounted on a common support 46, so as to move with the focussing lens during its adjustment.

The device illustrated in the drawings is operated in the following manner.

Before the laser 4 is energized, shutter 24 is moved to its blocking position, so that when the laser is energized the laser beam passes through lens 8 and apertured reflector 16 but impinges on the shutter, thereby protecting the patient from exposure to the laser beam. While the shutter is still in blocking position, the laser beam is aligned by using the X-axis and Y-axis adjustments 13 and 14. As these adjustments are made, the outer fringe of the laser beam, before reaching shutter 24, is reflected by the surfaces of reflector 16 bordering its aperture 18, and by reflectors 42, 44, to the sighting member 20, where it is focussed and produces a glow visible to the viewer via beam-splitter 35 and microscope 32. The focussed point on the sighting member 20 is thus transposed on the target area at the end of tube 6, which target area is also viewable via germanium window 10, reflector 40, beam-splitter 35, and microscope 32.

Thus, any manipulation or adjustment of the laser beam, by adjusting set screws 13 or 14, will be viewable as a focussed laser beam spot transposed on the target area, thereby enabling the operator to precisely align the laser beam on the target area in a real-time manner (i.e., while the laser is operating without subjecting the patient to the laser beam which is then blocked by shutter 24.

When the laser beam has been precisely aligned, piston 26 (FIG. 4) is actuated to move shutter 24 to its non-blocking position, enabling the center portion of the laser beam passing through aperture 18 to proceed via germanium window 10 to the target at the end of tube 6.

It is thus seen that the laser beam itself is used for alignment, rather than separate light sources, but the patient is not exposed to the laser beam until it has been exactly aligned on the point or spot to receive it. Morever, a sharper, better-defined beam is produced by the removal of the marginal fringe used for alignment purposes, thereby enabling fine cuts to be made with a minimum of damage to bordering tissue.

While the invention has been described with respect to laser scalpels used for surgery, it will be appreciated that features of the invention could also be used in other applications of lasers, such as in fine precision welding and material cutting. Further, these features could also be used in non-laser applications for example in precisely aligning other invisible high energy beams, with respect to a specific target.

Many other variations, modifications and applications of the illustrated embodiment will be apparent.

What is claimed is:

1. An alignment device for aligning a focussed beam of radiant energy with respect to a target comprising:
   means in the path of the focussed radiant energy beam for dividing said beam into a first portion and a second portion, said beam dividing means being formed as an aperture having a diameter smaller than the diameter of the radiant energy beam which permits the first portion of the beam to pass therethrough to the target and reflects the remainder of said radiant energy beam to form said second portion of the beam;
   a shutter for selectively intercepting said first portion of the beam between said beam dividing means and said target;
   a sighting member intercepting said second portion of the beam;
   an optical system for viewing the sighting member and the target with said sighting member and said target imaged on one another; and
   means for adjusting the position of said first portion of the beam on said target by adjusting the position of said second portion of the beam on said sighting member while said sighting member and said target are imaged on one another.

2. A device according to claim 1, wherein the optical system comprises an eyepiece having an axis that is parallel to, but laterally spaced from the direction of propagation of the radiant energy beam and is perpendicular to a line passing from the sighting member through the beam dividing means.

3. A device according to claim 2 wherein the optical system further comprises a beamsplitter disposed at the intersection of the eyepiece axis and the line passing from the sighting member through the beam dividing means, said beamsplitter including a reflecting surface at an angle of 45° with respect to both said axis and line to reflect the light from the sighting member to the eyepiece.

4. A device according to claim 3, further comprising an artificial light source disposed on the side of the beam splitter opposite to said reflecting surface thereof.

5. A device according to claim 3, further comprising a window between the shutter and the target, which window is transparent to the wave length of the radiant energy beam and is reflective with respect to other wave lengths.

6. A device according to claim 5 wherein said window is a germanium window and is disposed at 45° to the direction of propagation of the radiant energy beam to the target; and wherein the device further includes an additional reflector disposed at the intersection of the eyepiece axis and a line from the germanium window perpendicular to the eyepiece axis, said additional reflector being at a 45° angle with respect to said latter line and eyepiece axis.

7. A device according to claim 1, wherein the radiant energy beam is a laser beam in which the major portion of the beam energy is present in the center of the beam cross-section and is focussed to a fine point on the target, while a minor portion of the beam energy is present on the outer marginal fringe and is reflected by the beam dividing means to the sighting member.

8. A device according to claim 7, wherein the radiant energy beam is about 11mm. in diameter at incidence on said beam dividing means and the aperture in the beam dividing means is about 5mm. in diameter.

9. A device according to claim 1, further comprising means for moving the shutter into the path of the radiant energy beam to block same from travelling to the target, or out of the path of the radiant energy beam to permit same to travel to the target.

10. A device according to claim 9, wherein the shutter includes a heat sink effective to receive the intercepted radiant energy beam when the shutter is in blocking position.

11. A device according to claim 9, wherein said means for moving the shutter comprises a piston movable in a cylinder against the bias of a spring, said cylinder including means for varying the fluid pressure therein to move the piston, said shutter being carried by the piston.

12. A device according to claim 1, wherein said sighting member is a screen, which glows when impinged by the radiant energy beam.

13. The combination of a manipulatable laser and an alignment device in accordance with claim 1.

14. An endoscope for use with manipulatable lasers including an alignment device in accordance with claim 1.

15. A device according to claim 1, further comprising a window between the shutter and the target, which window is transparent to the wavelength of the radiant energy beam and is reflective with respect to visible light; and means in said optical system for viewing the target via the visible light reflected by said window.

16. A device according to claim 1, wherein at least one of the sighting member and the target is viewed in light which is different from that of said radiant energy beam.

17. A device according to claim 1, wherein said optical system further includes a folded reflector arrangement having a pair of reflectors between the sighting member and the beam dividing means each disposed to reflect the radiant energy beam 90°.

18. A method for aligning a focussed beam of radiant energy with respect to a target which comprises:
dividing said beam into a first portion and a second portion by a beam dividing means formed as an aperture having a diameter smaller than the diameter of the radiant energy beam which permits the first portion of the beam to pass therethrough to the target and reflects the remainder of said radiant energy beam to form said second portion of the beam;
selectively intercepting said first portion of the beam as it travels to said target;
intercepting the second portion of the beam with a sighting member;
simultaneously viewing the sighting member and the target with said sighting member and said target imaged on one another; and
adjusting the position of said first portion of the beam on said target by adjusting the position of said second portion of the beam on said sighting member as shown to be necessary by said viewing.

19. A method according to claim 18, further comprising the steps of:
directing the first portion of the beam through a window which is transparent to the wavelength of said beam but is reflective to visible light; and
viewing the target via the visible light reflected by said window.

20. A method according to claim 18, wherein at least one of the sighting member and the target is viewed in light which is different from that of said radiant energy beam.

21. An alignment device for aligning a beam of radiant energy with respect to a target comprising:
means in the path of the radiant energy beam for dividing said beam into a first portion which is directed toward the target and a second portion;
a shutter for selectively intercepting said first portion of the beam between said beam dividing means and said target;
a sighting member intercepting said second portion of the beam;
means for adjusting the position of said first portion of the beam on said target and the position of said second portion of the beam on said sighting member comprising an adjustable focussing lens in the path of the radiant energy beam before it is incident on the beam dividing means; and
an optical system for viewing the sighting member and the target with said sighting member and target imaged on each other, said optical system having at least one lens rigidly coupled to the focussing lens to move therewith during the adjustment of the focussing lens.

22. A device according to claim 21 wherein at least one of the sighting member and the target is viewed in light which is different from that of said radiant energy beam.

23. A method for aligning a beam of radiant energy with respect to a target which comprises:
dividing said beam into a first portion which is directed toward the target and a second portion;
selectively intercepting said first portion of the beam as it travels to said target;
intercepting the second portion of the beam with a sighting member;
adjusting the position of said first portion of the beam on said target and the position of said second portion of the beam on said sighting member by an adjustable focussing lens in the path of the radiant energy beam before it is incident on the beam dividing means; and
viewing the sighting member and the target with said sighting member and target imaged on each other by an optical system having at least one lens rigidly coupled to the focussing lens to move therewith during the adjustment of the focussing lens.

24. A method according to claim 23, wherein at least one of the sighting member and the target is viewed in light which is different from that of said radiant energy beam.

25. An alignment device for aligning a beam of radiant energy with respect to a target comprising:
means in the path of the radiant energy beam for dividing said beam into a first portion which is directed toward the target and a second portion;
a shutter for selectively intercepting said first portion of the beam between said beam dividing means and said target;
a sighting member intercepting said second portion of the beam;

an optical system for viewing the sighting member and the target with said sighting member and said target imaged on one another, said optical system comprising means for viewing the target even when said first portion of the beam is intercepted by said shutter; and means for adjusting the position of said first portion of the beam on said target by adjusting the position of said second portion of the beam on said sighting member while said sighting member and said target are imaged on one another, whereby the position of the first portion of the beam on the target can be adjusted even when it is intercepted by said shutter.

26. An alignment device according to claim 25, wherein said viewing means comprises a reflector between said shutter and said target in the path of the first portion of the radiant energy beam but transparent thereto which reflects light as it travels from said target and a beamsplitter in the path of the light reflected from said reflector and light from said sighting member, said beamsplitter combining the light from said sighting member and the light from said target.

27. A device according to claim 26, wherein the beam dividing means is formed as an aperture having a diameter smaller than the diameter of the radiant energy beam which permits the first portion of the beam to pass therethrough to the target and reflects the remainder of said radiant energy beam to form said second portion of the beam and the light from said sighting member passes through the aperture of the beam dividing means to the beamsplitter.

28. A device according to claim 25, wherein the optical system comprises an eyepiece having an axis that is parallel to, but laterally spaced from the direction of propagation of the radiant energy beam and is perpendicular to a line passing from the sighting member through the beam dividing means, and a beamsplitter disposed at the intersection of the eyepiece axis and the line passing from the sighting member through the beam dividing means, said beamsplitter including a reflecting surface at an angle of 45° with respect to both said axis and line to reflect the light from the sighting member to the eyepiece.

29. An alignment device according to claim 25, wherein at least one of the sighting member and the target is viewed in light which is different from that of said radiant energy beam.

30. A method for aligning a beam of radiant energy with respect to a target which comprises:

dividing said beam into a first portion which is directed toward the target and a second portion;

selectively intercepting said first portion of the beam as it travels to said target;

intercepting the second portion of the beam with a sighting member;

viewing the sighting member and the target with said sighting member and said target imaged on one another even when said first portion of the beam is intercepted; and adjusting the position of said first portion of the beam on said target by adjusting the position of said second portion of the beam on said sighting member while said sighting member and said target are imaged on one another, whereby the position of the first portion of the beam on the target can be adjusted even when it is intercepted.

31. A method according to claim 30, wherein the viewing step includes the steps of reflecting light from said target out of the path of the first portion of the radiant energy beam and combining the reflected light with light from said sighting member.

32. A method according to claim 30, wherein at least one of the sighting member and the target is viewed in light which is different from that of said radiant energy beam.

* * * * *